United States Patent
Gelling et al.

(10) Patent No.: US 6,274,773 B1
(45) Date of Patent: Aug. 14, 2001

(54) PROCESS FOR THE CONTINUOUS PREPARATION OF ALKYL 5-FORMYLVALERATE COMPOUNDS USING HOMOGENEOUS RHODIUM HYDROFORMYLATION CATALYSTS

(75) Inventors: Onko J. Gelling, Stein; Peter C. Borman, Geleen, both of (NL)

(73) Assignees: DSM, Heerlen (NL); E.I. DuPont De Nemours & Co., Wlimington, DE (US)

( * ) Notice: Subject to any disclaimer, the term of this patent is extended or adjusted under 35 U.S.C. 154(b) by 0 days.

(21) Appl. No.: 09/304,668

(22) Filed: May 4, 1999

Related U.S. Application Data

(63) Continuation of application No. PCT/NL97/00596, filed on Oct. 30, 1997.
(60) Provisional application No. 60/032,678, filed on Dec. 9, 1996.

(30) Foreign Application Priority Data

Nov. 4, 1996 (EP) .................................. 96203071

(51) Int. Cl.⁷ .................................. C07C 45/50
(52) U.S. Cl. ............ 568/454; 568/85; 568/449; 568/451
(58) Field of Search .................. 568/454, 449, 568/85, 451

(56) References Cited

U.S. PATENT DOCUMENTS

| | | |
|---|---|---|
| 4,169,861 | 10/1979 | Hughes . |
| 4,748,261 | 5/1988 | Billig et al. . |
| 4,769,498 | 9/1988 | Billig et al. . |
| 5,235,113 | 8/1993 | Sato et al. . |

FOREIGN PATENT DOCUMENTS

| | | |
|---|---|---|
| 4204808 A1 * | 8/1993 | (DE) . |
| 0 518 241 | 12/1992 | (EP) . |
| 0 556 681 | 8/1993 | (EP) . |
| 0 590 613 | 4/1994 | (EP) . |
| 95/18089 | 7/1995 | (WO) . |

* cited by examiner

*Primary Examiner*—Gary Geist
*Assistant Examiner*—Robert W. Deemie
(74) *Attorney, Agent, or Firm*—Pillsbury Winthrop LLP

(57) ABSTRACT

Process for the continuous preparation of an alkyl 5-formylvalerate by reacting an alkyl-3-pentenoate with carbon monoxide and hydrogen by hydroformylation using a catalyst system comprising rhodium or iridium and a multidentate organic phosphite ligand according to the general formula:

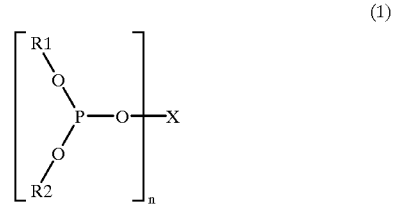

(1)

in which n is 2–6, X is an n-valent organic bridging group, and in which the end groups $R^1$–$R^2$ are monovalent aryl groups, wherein the process is carried out in the presence of an acid compound having a pKa between 1 and 12 measured in water at 18° C.

14 Claims, No Drawings

PROCESS FOR THE CONTINUOUS PREPARATION OF ALKYL 5-FORMYLVALERATE COMPOUNDS USING HOMOGENEOUS RHODIUM HYDROFORMYLATION CATALYSTS

This is a Continuation of International Appln. No. PCT/NL97/00596 filed Oct. 30, 1997.

This application claims benefit of U.S. Provisional Application No. 60/032,678, filed Dec. 9, 1996.

The invention relates to a process for the continuous preparation of an alkyl 5-formylvalerate by reacting an alkyl 3-pentenoate with carbon monoxide and hydrogen by hydroformylation using a catalyst system comprising rhodium or iridium and a multidentate organic phosphite ligand according to the general formula:

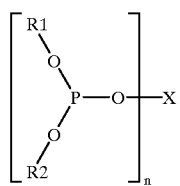

in which n is 2–6, X is an n-valent organic bridging group and in which the end groups $R^1$–$R^2$ are monovalent aryl groups.

Such a process is described in WO-A-9518089. This patent application describes a process in which methyl-5-formylvalerate is prepared with a selectivity of 80% starting from methyl 3-pentenoate using a catalyst system consisting of rhodium and a tetravalent organic phosphite, in which $R^1$ and $R^2$ are phenyl groups substituted on the ortho and para position with a tert-butyl group and X is a group according to C—($CH_2$—)$_4$.

A disadvantage of this process is that the catalyst is not stable over a prolonged period of time. For example after some days of continuous operation the reaction rate will continuously drop due to deactivation of the catalyst. Deactivation of the catalyst is not desired when performing a continuous hydroformylation process especially in a large scale process.

The object of this invention is a process with a reduced catalyst deactivation.

This object is achieved in that the process is carried out in the presence of an acid compound having a pKa between 1 and 12 when measured in water of 18° C.

It has been found that the catalyst activity can be stabilized over a prolonged period of time when such an acid is present. Moreover in spite of the addition of an acid no significant amount of 5-formylvaleric acid is formed due to acid catalyzed hydrolysis of the ester group of the alkyl 5-formylvalerate.

The addition of an acid, such as aromatic compounds substituted with carboxylic or hydroxy groups, to a rhodium-organophosphite complex catalyzed hydroformylation process is known from EP-A-590613. The organophosphite ligands described in this application however differ from the ligand according to formula (1) in that the end groups of the bisphosphite ligands are connected to each other, forming a cyclic structure. The cyclic structure is present when two of the organic groups (groups like $R^1$ and $R^2$) are connected with each other. According to EP-A-590613 the catalyst deactivation is caused by the presence of this unique cyclic end group structure. The degradation product of the ligand described in EP-A-590613 is referred to as "the poisoning phosphite" having the corresponding cyclic structure. Such a poisoning phosphite however cannot be formed when a phosphite according to formula (1) is used.

The acid is preferably present in an amount of 0.05 to 20 wt % during the hydroformylation reaction. More preferably between 0.1 and 1 wt %.

The acid can be any acid with a pKa between 1 and 12 and preferably between 2.5 to 10, measured in water of 18° C. Examples of suitable acids are aromatic carboxylic acids, for example optionally substituted benzoic acid, p-chlorobenzoic acid, phthalic acid, aliphatic carboxylic acids, for example dicarboxylic acids having between 2–20 carbon atoms, for example adipic acid, glutaric acid and fumaric acid, mono carboxylic acids, for example valeric acid, butynic acid, decanoic acid, mono methyl adipate, mono methyl glutarate, phenols, for example phenol, cresol, p-methylphenol, bisphenols, bis-β-naphthol, dihydroxy naphthalene. Preferably the acid has a normal boiling point higher than 200° C.

$R^1$ and $R^2$ in formula (1) are preferably the same or different monovalent aryl groups with 6 to 20 carbon atoms. It is to be understood that the various $R^1$ and $R^2$ groups can be different from each other. Preferably all $R^1$ and $R^2$ groups are the same because the resulting ligands are more readily available. Preferably $R^1$ and $R^2$ are monovalent aryl groups, for example phenyl, containing at least one group, $R^3$, other than hydrogen in an ortho position relative to the oxygen atom, where $R^3$ is a $C_1$ to $C_{20}$ alkyl or $C_6$–$C_{20}$ aryl group and preferably a $C_1$–$C_6$ alkyl group. Other preferred monovalent aryl groups for $R^1$ and $R^2$ are monovalent fused aromatic ring systems with 2 or more rings having 10–20 carbon atoms. $R^1$ and $R^2$ can optionally be further substituted with for example Cl–C10 alkyl, $C_6$–$C_{20}$ aryl, $C_1$–$C_{10}$ alkoxy, $C_6$–$C_{20}$ aryloxy groups, triarylsilyl, trialkylsilyl, carboalkoxy, carboaryloxy, alkylcarbonyl, arylcarbonyl, oxazole, amide, amine or a nitrile or halogen groups, for example F, Cl or Br.

When the aryl groups $R^1$ and $R^2$ are substituted with at least one $R^3$-group in the ortho-position relative to the phenolic oxygen atom, higher linear selectivity is observed using these ligands in a hydroformylation process. Examples of these $R^3$ groups are methyl, ethyl, propyl, isopropyl, isobutyl, tert-butyl or n-butyl. $R^3$ is preferably only one bulky group, having a steric hinderance of isopropyl or greater. When less bulky substituents are used preferably both ortho positions are substituted with these groups. Preferably $R^1$ and $R^2$ are 2-isopropylphenyl or 2-tert-butylphenyl groups.

Another preferred class of aryl groups for $R^1$ and $R^2$ are fused aromatic ring systems with 2 or more rings having 10 to 20 carbon atoms which do not necessarily have to be substituted at the ortho position (on the carbon atom adjacent to the carbon atom which is bonded to the oxygen atom in formula (1)) with groups other than hydrogen. It has been found that when $R^1$ and/or $R^2$ is such an unsubstituted aromatic ring system, high catalyst activity, a high selectivity to terminal aldehyde and a high linearity can be achieved. Examples of such fused aromatic ring systems are phenanthryl, anthryl and naphthyl groups. Preferably 9-phenanthryl or 1-naphthyl groups are used.

X is preferably an organic group having between 1 and 40 carbon atoms, and more preferably between 4 and 40 carbon atoms. Bidentate ligands, having a bivalent bridging group (n=2), are most mentioned in the patent literature. Examples of bridging groups X can be found in U.S. Pat. No. 4,748, 261, EP-A-556681 and EP-A-518241. Preferably the bridging group X is such that the multidentate phosphite ligand can form a chelate-type complex with the metal employed (rhodium or iridium) during the reaction conditions. By a chelate type complex is meant that (substantially) at least two phosphorus atoms of a ligand molecule form a coordinated bond with one rhodium or iridium atom/ion. By a non-chelate-type complex is meant that only one phosphorus P atom of a ligand molecule forms a coordinated bond with one rhodium or iridium atom/ion. The choice of bridging group X of the ligand will determine whether a chelate-type complex can be formed in the reaction zone. Examples of bridging groups which result in a ligand which can form a chelate-type bridging group are for example described in WO-A-9518089. Preferably bridging group X has a structure according to formula (2) or (3):

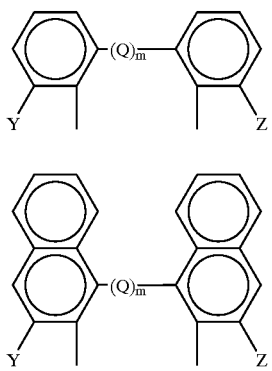

in which Q is —O—, —S— or a —CR$^4$R$^5$— divalent group and m is 0 or 1 and R$^4$ and R$^5$ is hydrogen or a methyl group and Y and Z hydrogen or organic groups containing at least one carbon atom, and more preferably containing 1–20 carbon atoms. Preferably m=0.

Preferably Y and Z are individually selected from the, group of alkyl, aryl, triarylsilyl, trialkylsilyl, carboalkoxy, carboaryloxy, aryloxy, alkoxy, alkylcarbonyl, arylcarbonyl, oxazole, amide, amine or a nitrile.

For Y and Z, the alkyl group is preferably a $C_1$–$C_{10}$ alkyl group, for example methyl, ethyl, propyl, isopropyl, butyl, tert-butyl, isobutyl, pentyl or hexyl. An example of a suitable triarylsilyl group is triphenylsilyl and examples of a suitable trialkylsilyl group are trimethylsilyl and triethylsilyl. Preferred aryl groups have 6 to 20 carbon atoms, for example phenyl, benzyl, tolyl, naphthyl, anthranyl or phenanthryl. Preferred aryloxy groups have 6 to 12 carbon atoms, for example phenoxy. Preferred alkoxy groups have 1 to 20 carbon atoms, for example methoxy, ethoxy, tert-butoxy or isopropoxy. Preferred alkylcarbonylgroups have 2 to 12 carbon atoms, for example methylcarbonyl, tert-butylcarbonyl. Preferred arylcarbonyl groups have 7 to 13 carbon atoms, for example phenylcarbonyl. Preferred amide groups contain a $C_1$–$C_4$ alkyl group and preferred amine groups contain two $C_1C_5$ alkyl groups.

Most preferably, Y and Z are individually a carboalkoxyl or a carboaryloxy group, —CO$_2$R$^6$, in which R$^6$ is a $C_1$–$C_{20}$ alkyl group or a $C_6$–$C_{12}$ aryl group and preferably a $C_1$–$C_8$ alkyl group. Examples of suitable R$^6$-groups are methyl, ethyl, propyl, isopropyl, n-butyl, tert-butyl, isobutyl, phenyl and tolyl. Even more preferably both Y and Z are the same carboaryloxy and more preferably the same carboalkoxyl group because the resulting ligands are more easily obtainable.

The group according to formula (2) or (3) can optionally be further substituted with other groups, for example halogen, for example Cl or F or one of the substituents which may be present on the bridging group as described above.

More preferably the bridging group is a 2,2'-dihydroxy-1,1'-binaphthalene bridging group according to formula (3) substituted as described above. It has been found that when using these ligand compounds a high selectivity to alkyl 5-formylvalerate can be achieved at a high reaction rate. The ligands having bridging groups according to formula (3) may be prepared by a variety of methods known in the art, for example, see descriptions in U.S. Pat. Nos. 4,769,498; 4,688,651 and J. Amer. Chem. Soc., 1993, 115, 2066. The organic bidentate phosphite compounds according to the invention can be prepared with the 3- or 3,3'-substituted 2,2'-dihydroxy-1,1'-binaphthalene bridging compounds. The binaphthol bridging compounds can be prepared by procedures as described in Tetrahedron Lett. 1990, 31(3), 413–416 or in J. Am. Chem. Soc. 1954, 76, 296 and Org. Proc. Prep. International, 1991, 23, 200. The phosphite compounds can be prepared by using the process as described in the earlier mentioned U.S. Pat. No. 5,235,113 to couple these binaphthol bridging compounds with phosphorochloridites, (R$^1$O)(R$^2$O)PCl, prepared by treating R$^1$OH and/or R$^2$OH with PCl$_3$.

Examples of phosphite ligands which can be used in the process according to this invention are shown below. In the formula's the following fragments have the following meaning.

/=methyl,
L=ethyl,
Ph=phenyl,
⊥=isopropyl,
Me=methyl,
+=tert-butyl

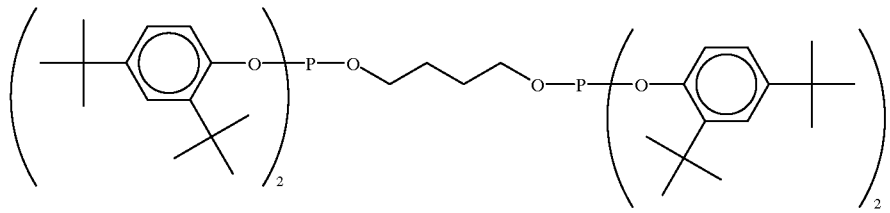

-continued
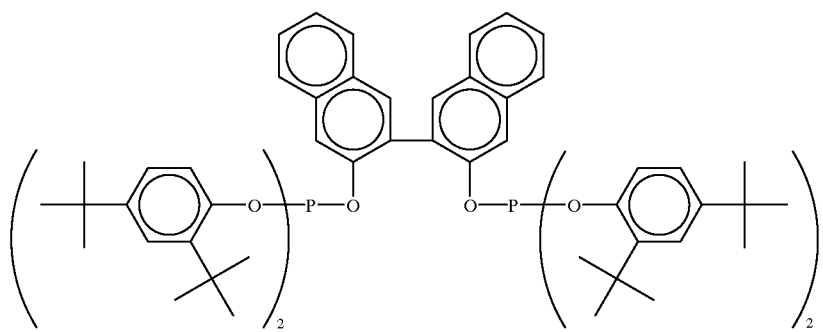
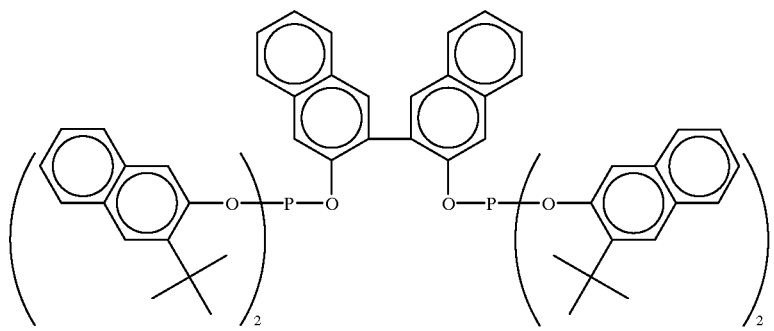
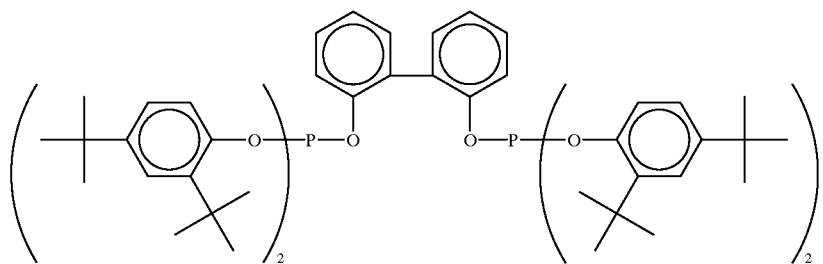
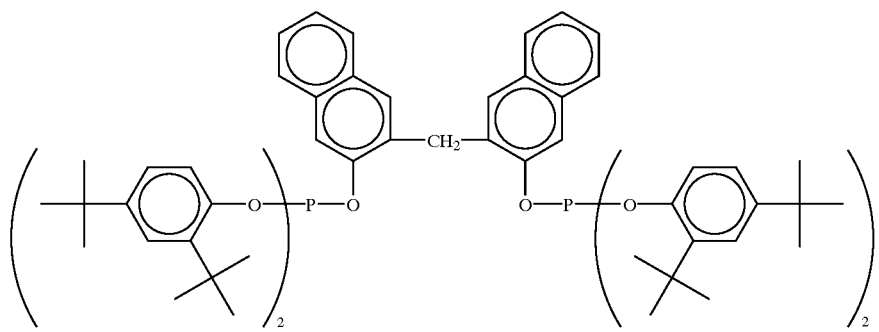
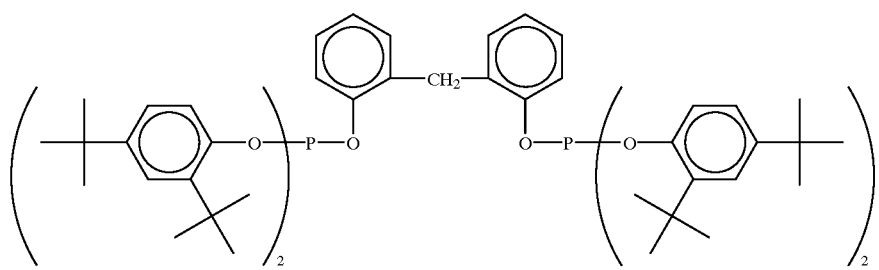

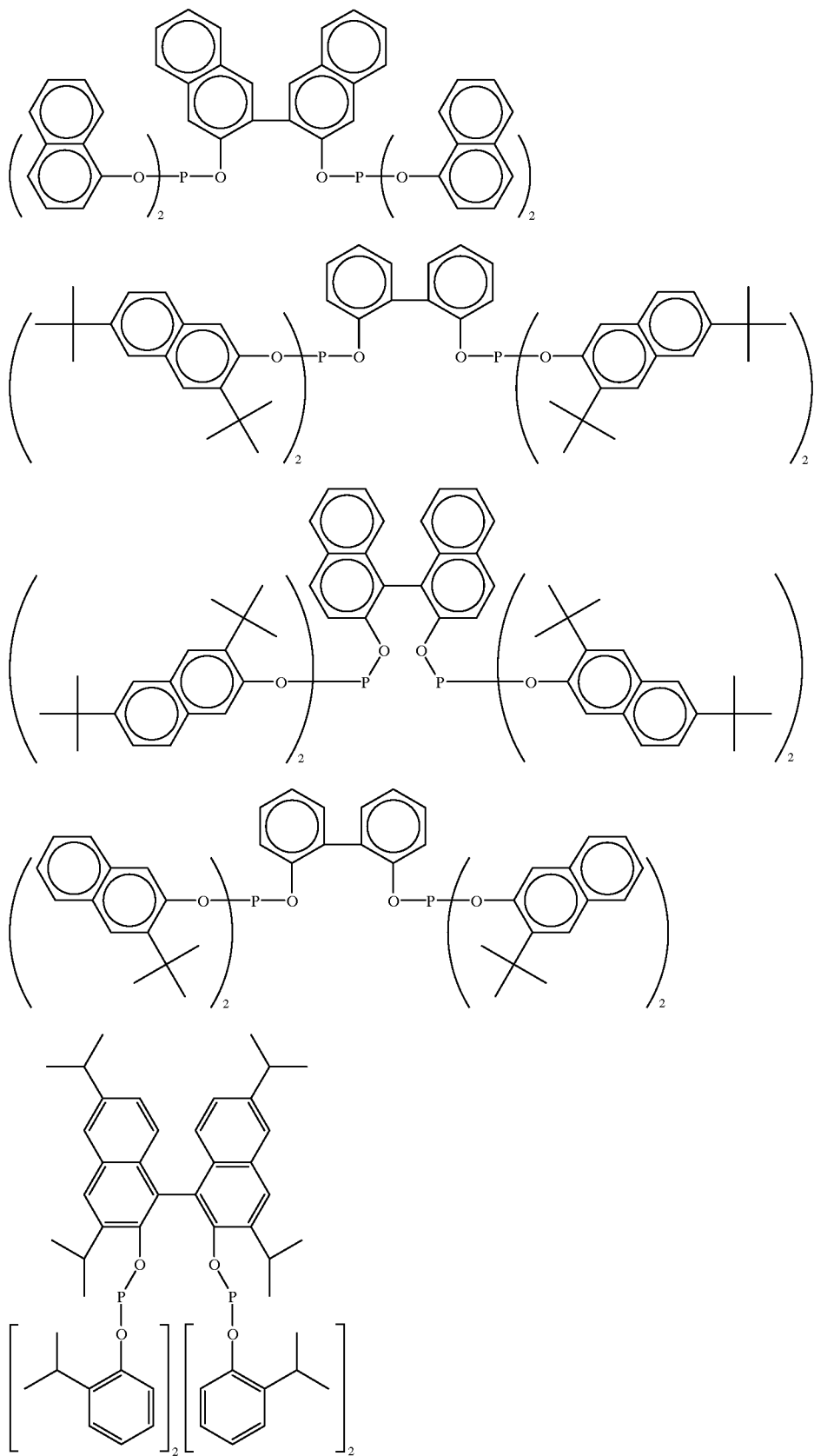

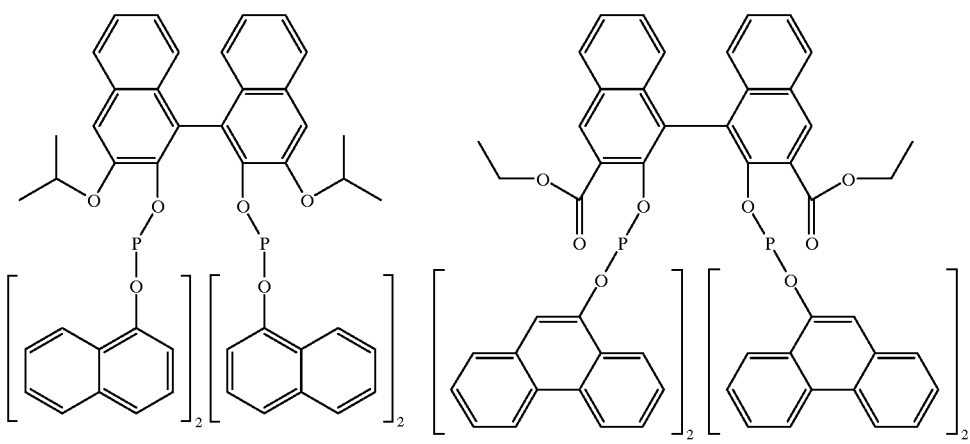
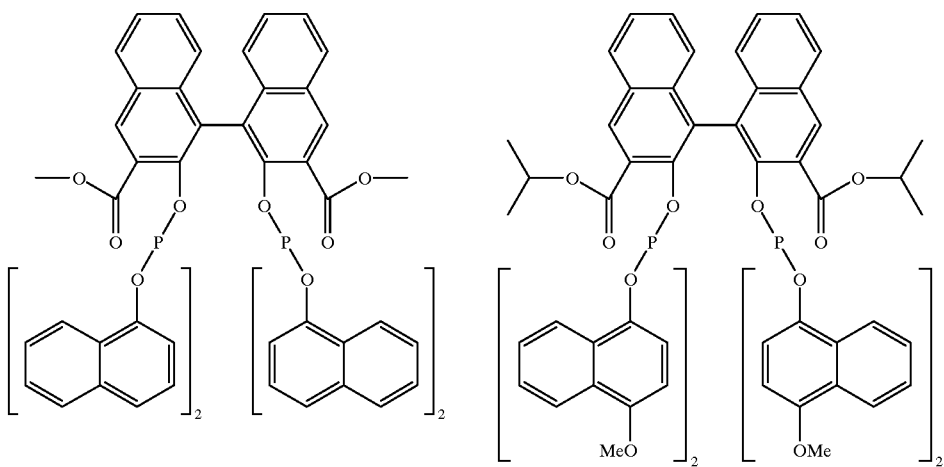
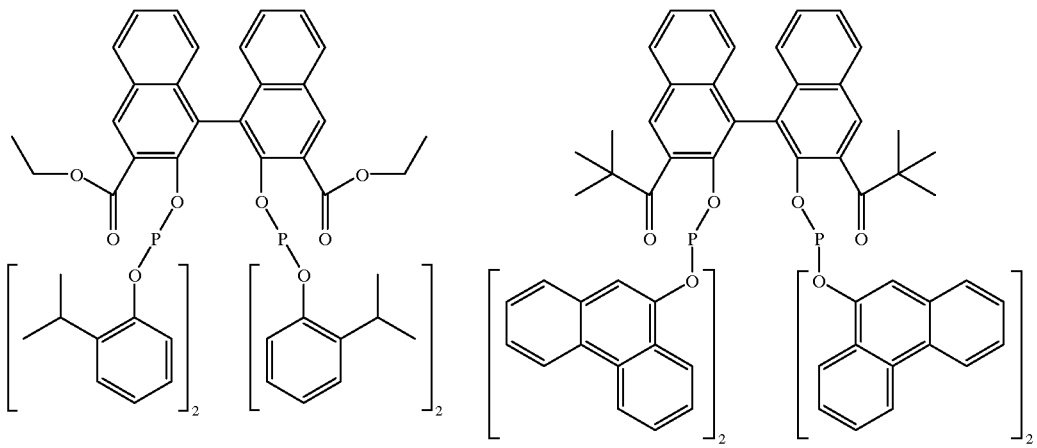

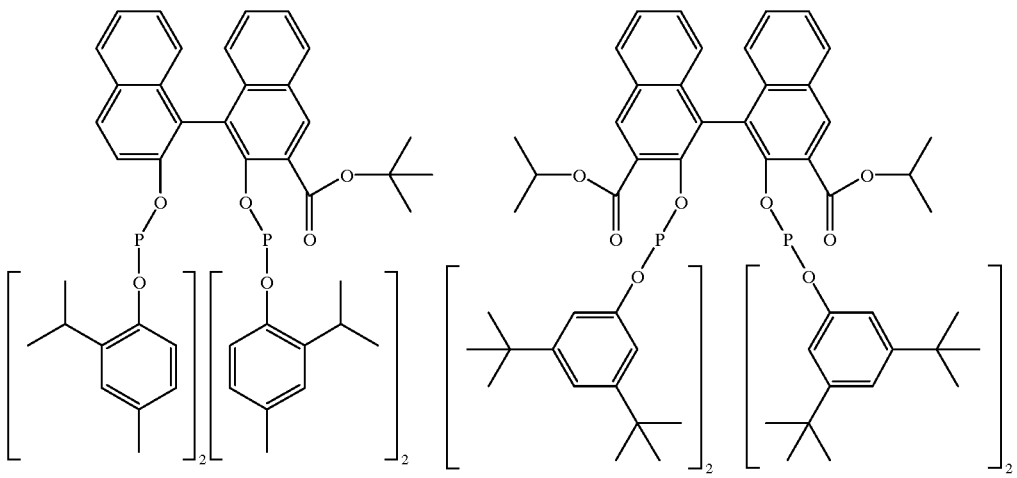
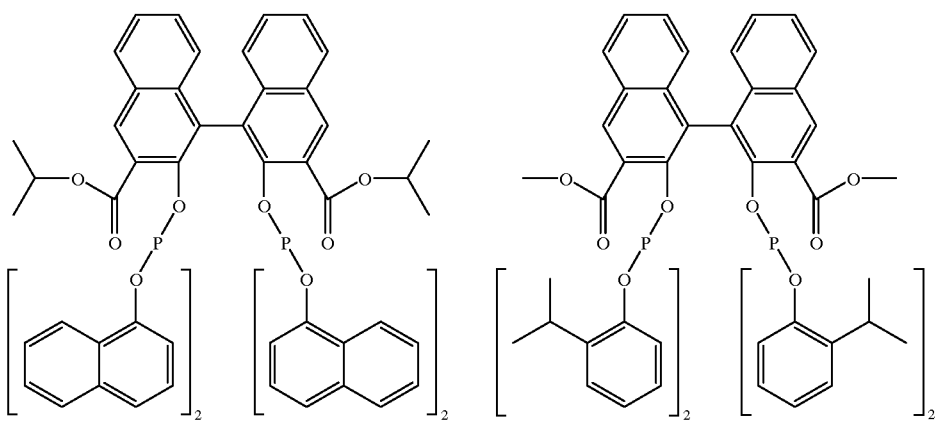
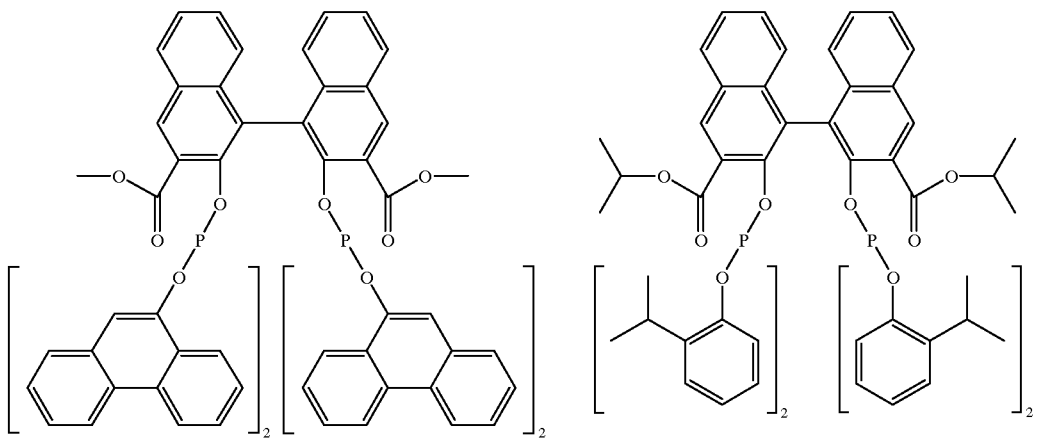

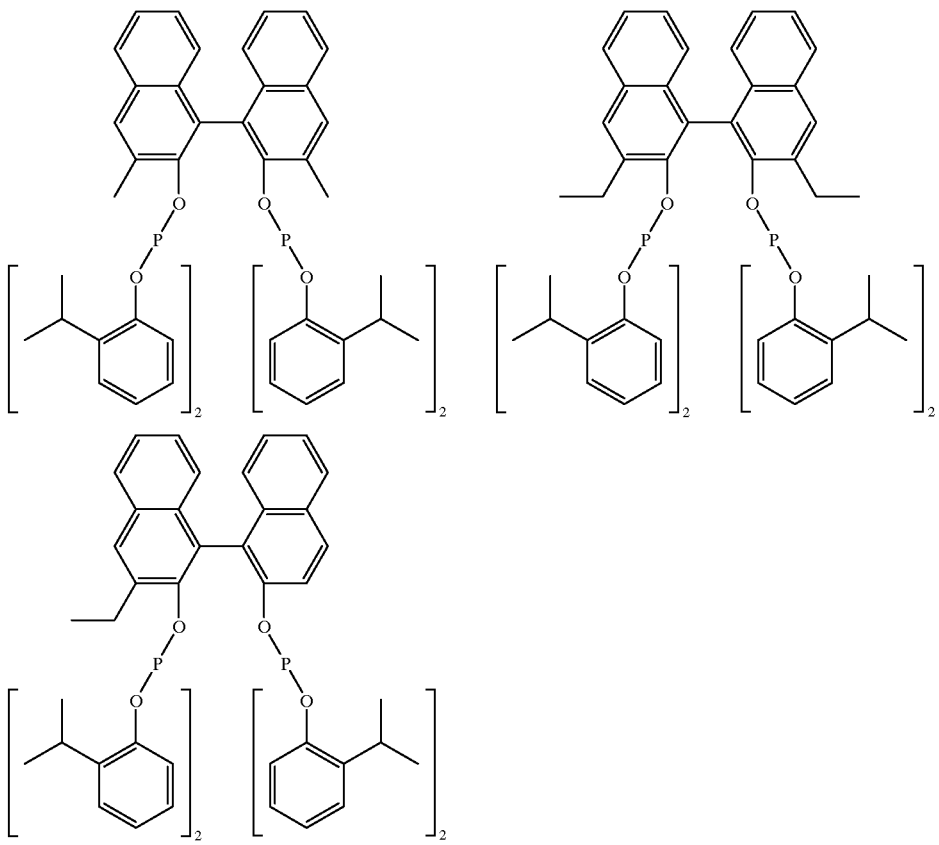

The catalyst system used in the process according to this invention can be prepared by mixing a suitable rhodium or iridium compound with the phosphite ligand, optionally in a suitable solvent, in accordance with well-known complex-forming methods. The solvent will generally be the solvent used in the hydroformylation. Suitable rhodium and iridium compounds are for example hydrides, halides, organic acid salts, acetylacetonates, inorganic acid salts, oxides, carbonyl compounds and amine compounds of these metals. Examples of suitable catalyst precursors are, for example, $Ir(CO)_2(acac)$, $Ir_4(CO)_{12}$, $RhCl_3$, $Rh(NO_3)_3$, $Rh(OAc)_3$, $Rh_2O_3$, $Rh(acac)(CO)_2$, $Rh(CO)_2(DPM)$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$, (wherein "acac" is an acetylacetonate group; "Ac" is an acetyl group; "COD" is 1,5-cyclooctadiene; and "Ph" is a phenyl group, DPM is 2,2,6,6-tetramethyl-3,5-heptanedionate group). However, it should be noted that the rhodium and iridium compounds are not necessarily limited to the above listed compounds.

The metal is preferably rhodium.

In order to further improve the stability of the catalyst system it is preferred to add some organophosphorous compound which has a coordination strength to rhodium less than the multidentate phosphite ligand. Examples of suitable organophosphorous compounds are phosphites and monodentate phosphines. The presence of the organophosphorous compounds avoids oxidation of the phosphite ligand.

Preferred phosphine compounds have a steric parameter θ of between 160°–220°. This preferred monodentate phosphine can be represented by the general formula $P(R')_3$, where the R' groups are organic groups that are chosen so that the steric parameter θ of the phosphine is between 160° and 220°, preferably between 170° and 210°. The steric parameter θ is the top angle of a cylindrical cone, centred at 2.28 Å($10^{-10}$ m) from the centre of the phosphorus atom, which just touches the Van der Waals radii of the outer atoms of the R' substituents of a symmetrical $P(R')_3$-phosphine (see also "Chemical Reviews, 1977, Volume 77, pp. 313–348" by C. A. Tolman and U.S. Pat. No. 4,169,861).

The organic group R' of the $PR'_3$ phosphine is preferably an aliphatic, alicyclic or aromatic group with 1–20 carbon atoms, preferably 5–12 carbon atoms, and the three R' groups may be the same or different. The R' group may contain one or more hetero atoms, for example oxygen, nitrogen or a halogen.

Examples of monodentate phosphines according to the invention are tri(isopropylphosphine), tri(sec-butyl) phosphine, tribenzylphosphine, tricyclohexylphosphine, dicyclohexylphenylphosphine, di(t-butyl)phenylphosphine, trineopentylphosphine, tri(t-butyl)phosphine, tri-(o-hydroxyphenyl)phosphine, tri(o-methoxyphenyl)phosphine, tri(pentafluorophenyl)phosphine, tri(o-tolyl)phosphine and trimesityl-phosphine. A mixture of two or more of these compounds is also suitable for use as the monodentate phosphine. Preferably, the $PR'_3$ phosphine is trineopentylphosphine, tri(t-butyl)phosphine or tri(o-tolyl) phosphine.

Most preferably, tri(o-tolyl)phosphine is used as the monodentate phosphine in the process according to the invention. Tri(o-tolyl)phosphine is cheap, readily obtainable and shows a high effectiveness in small amounts.

Examples of stabilizing phosphite compounds are triphenylphosphite, tri(p-tolyl)phosphite, tri(isopropyl) phosphite, tri(o-tolyl)phosphite, tri(o-isopropylphenyl)

phosphite, tri(t-butyl)phosphite, tri(o-t-butylphenyl) phosphite, tri(2,6-dimethylphenyl)phosphite, tri(2,4-di-t-butylphenyl)phosphite, pentaerythyl -(2,4-di-t-butylphenylphosphite) and the commercially available Ultranox and Weston phosphite compounds of General Electric Plastics. Examples of preferred stabilizing phosphite compounds are tri(o-t-butylphenyl)phosphite, tri(2,6-dimethylphenyl)phosphite and tris (2,4-di-t-butylphenyl) phosphite.

The alkyl group of the starting alkyl-3-pentenoate ester compound preferably has 1–20 and more preferably 1–6 carbon atoms. Examples of $C_1$–$C_6$ alkyl-3-pentenoates are methyl-, ethyl-, propyl-, isopropyl-, tert-butyl-, pentyl- and cyclohexyl-3-pentenoate. Preferably methyl- or ethyl 3-pentenoate is used as starting compound because these compounds are more readily available. The alkyl 3-pentenoate ester compound may be present in mixtures containing also alkyl 2- and/or alkyl 4-pentenoate compounds. The alkyl pentenoate mixture may have a composition of 0–10% alkyl 2-pentenoate, 0–30% alkyl 4-pentenoate and 60–100% 3-pentenoate in which the total of alkyl pentenoates add up to 100%.

The alkyl 5-formylvalerate can advantageously be used in the preparation of ε-caprolactam or adipic acid, which are precursors for respectively Nylon-6 and Nylon-6.6.

The hydroformylation process according to the invention can be performed as described below. The temperature is preferably between room temperature and 200° C., and more preferably from about 50 to 150° C. The pressure may vary from atmospheric pressure (0.1 MPa) to 20 MPa, preferably from 0.15 to 10 MPa and more preferably from 0.2 to 1 MPa. The pressure is generally equal to the combined hydrogen and carbon monoxide partial pressure. Extra inert gasses may however be present. The molar ratio hydrogen:carbon monoxide is generally between 10:1 and 1:10 and preferably between 6:1 and 1:2.

The amount of rhodium or iridium (compound) is not specially limited, but is optionally selected so that favorable results can be obtained with respect to catalyst activity and process economics. In general, the concentration of rhodium or iridium in the reaction medium is between 10 and 10,000 ppm and more preferably between 50–1000 ppm, calculated as free metal.

The molar ratio of bidentate phosphite ligand to rhodium or iridium is generally from about 0.5 to 100 and preferably from 1 to 10 (mol ligand/mol metal) and most preferably less than 1.2. Preferably the ratio is higher than 1.05. Small deviations in ligand or rhodium concentration will then not automatically result in a lower yield to alkyl 5-formylvalerate. It has been found that by performing the process with such a slight molar excess of ligand to rhodium (or iridium) the ligand degradation, due to other causes than oxidation, is decreased. When performing the process with a slight excess of ligand to rhodium (or iridium) it will be preferred to monitor the concentration (and degradation) of the ligand during the course of the continuous process and add fresh ligand in order to remain in the preferred ranges of operation.

The choice of solvent is not critical provided the solvent is not detrimental to catalyst, reactant, and/or product. The solvent may be the mixture of reactants, such as the starting unsaturated compound, the aldehyde product and/or by-products. Suitable solvents include saturated hydrocarbons, for example kerosene, mineral oil or cyclohexane, ethers, for example diphenyl ether tetrahydrofuran or a polyethyleneglycol, for example Carbowax TM-400, ketones, for example methyl ethyl ketone or cyclohexanone, nitrites, for example 2-methylglutaronitrile or benzonitrile, aromatics, for example toluene, benzene or xylene, esters, for example methyl valerate or caprolactone, Texanol® (Union Carbide), or dimethylformamide, sulfones (for example tetramethylenesulfone). The addition of extra water (apart from the water formed in the process) is not preferred.

The hydroformylation can be performed in any kind of reactor which enables the reactants to be well mixed with the catalyst system and carbon monoxide and hydrogen.

The continuous process is preferably performed by continuously removing part of the liquid reaction medium from the hydroformylation reactor. This mixture comprises the alkyl 5-formylvalerate, the catalyst system, optionally the solvent, by-products, unreacted alkyl pentenoate and carbon monoxide and hydrogen dissolved in said medium. In a first step any carbon monoxide and hydrogen is removed from this mixture by reducing the pressure in for example a flash operation. This carbon monoxide and hydrogen may be reused in the hydroformylation. The alkyl 5-formylvalerate, unreacted alkyl pentenoate and low boiling by-products, for example alkylvalerate, branched aldehydes and any formed water are preferably separated from the catalyst system in one or more distillation operations performed at reduced pressure. The pressure is preferably low enough to be able to perform the distillation at a temperature below 100° C. An example of a distillation unit is a rolled film evaporator. Another suitable separation method is membrane separation as for example described in WO-A-9634687. Other methods of performing this separation are of course also possible. The catalyst system is recycled to the hydroformylation reactor. Preferably any unreacted alkyl pentenoates are also recycled to the hydroformylation reactor. Any alkyl 2-pentenoate present is preferably converted to alkyl-3- or 4-pentenoate in a separate isomerization step before feeding the alkyl pentenoate mixture to the hydroformylation reactor. An example of such an isomerization process is described in U.S. Pat. No. 4,874,889.

The products which are separated from the catalyst system are preferably separated from each other by distillation. Other separation techniques, for example extraction and crystallization, are however also possible. The alkyl 5-formylvalerate is preferably separated from its branched by-products, alkyl 3- and alkyl 4-formylvalerate, by distillation. These branched products can be burned or decarbonylated to the alkyl pentenoate starting compound by well known processes.

It has been found that it is very advantageous to contact the recirculating catalyst system with a basic compound, for example a basic resin, as described in WO-A-8503702 and EP-A-285136. It has been found that specific acids may form due to degradation of the phosphite ligand in the process according to the invention. It is believed, without being bound to any theory, that traces of these specific acids have an detrimental effect on the stability of the phosphite ligand. It is therefore advantageous to separate these acid compounds from the continuously circulating catalyst system to avoid a build up of these acids. The contacting with the basic compound may take place at any stage in which the catalyst composition is present. For example the reactor effluent can be contacted with the basic compound. Preferably the catalyst system is contacted with the basic compound after separating the aldehyde product from the catalyst system. Examples of basic compounds are metal oxides, for example CaO and MgO. Preferably heterogenic basic compounds are used and most preferably the basic compound is a resin having basic groups. Examples of possible basic groups are secondary or tertiary amine groups, according to -NHR or —NR$_2$, in which R is an organic group, preferably a C$_1$–C$_6$ alkyl groups, more preferably methyl.

Examples of commercially available resins which can be used are Amberlist A-21, A-22, A-23 and A-26 (Amberlist is a brand name of Rohm & Haas). Because of the use of this basic resin it is necessary to use an excess of the acid in the process according to the invention, compared to the basic sites present in the resin. It is anticipated that the acid will bind to the basic sites but will be replaced by stronger acids like the above described ligand degradation products (hydroxy phosphites) thereby liberating the weaker acid which are present in the process according to this invention.

Preferably, purge flows are present in the process to prevent an accumulation of by-products and the degradation products of the phosphite ligand complex. These purge flows mostly comprise an amount of the rhodium/phosphite catalyst system. The concentration of rhodium in such a purge flow will generally be higher than 100 ppm rhodium and lower than 2000 ppm rhodium. For a commercially interesting process it is necessary to recover the catalyst system comprising the rhodium/phosphite ligand complex from such a purge flow. The rhodium/phosphite ligand complex can advantageously by recovered from such purge flows using a membrane separation process as described in WO-A-9634687.

The invention will be elucidated with the following non-limiting examples.

EXAMPLE 1

A solution containing 5.6 grams of a bidentate phosphite ligand with structure:

(A)

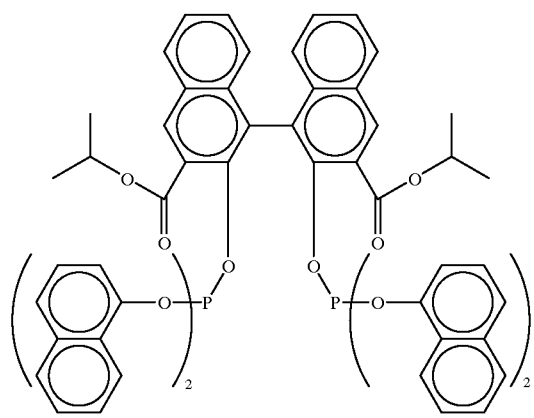

having a molweight of 1090 grams/mol, 1.10 grams of RhAcAc(CO)$_2$, 16 grams tri-ortho-tolyl phosphine and 576 grams of m-xylene was prepared. A Hasteloy-B reactor with a nominal volume of 1 L was pressurized with CO and H$_2$ to 1 MPa (CO/H$_2$=1 (mol/mol)). The reactor was charged with 200 grams of the catalyst solution and 300 grams of freshly distilled methyl-3-pentenoate (M3P), heated to 95° C. and left to for two hours while continuously feeding CO and H$_2$ in a 1:1 ratio at a flow rate of 30 Nl/hr each to the autoclave.

After these two hours a continuous feed to the autoclave of 90 grams/hr M3P and 80 grams/hr of catalyst solution was started originating from storage vessels containing these compounds. The catalyst solution feed was maintained until a total of 483 grams of solution was charged to the autoclave. The reactor pressure was subsequently reduced to 0.5 MPa. The level of liquid in the reactor was kept at a maximum of approximately 500 ml of liquid. Any excess liquid and any unreacted gasses will exit the reactor via a dip tube. This exit stream was let down to atmospheric pressure via a back pressure regulator and fed into a gas-liquid separator. The gas was—after passing through a condensor to remove condensables—vented. The liquid was collected in the bottom of the gas liquid separator from where it is fed through a control valve to a first rolled film evaporator operated at 90° C. In this evaporator most of the unreacted M3P, light by-products and a small part of the methyl formylvalerate (MFV) products were evaporated under vacuum (approximately 0.05 MPa). The liquid residue obtained in the first evaporation was passed through a column filled with an amount of 7 grams of a weakly basic Amberlist A21 (ion exchange) resin. From there it was pumped to a second rolled film evaporator. In this evaporator the remainder of the unreacted M3P and light byproducts and part of the methylformylvalerate product was evaporated.

The residue of the second evaporator was pumped back into the reactor thereby closing the loop. The temperature and the pressure of both evaporators were adjusted such that a constant liquid inventory of 1200 ml (if calculated back to the reactor) is maintained in the whole set-up as described above. Approximately 4 hours after starting the M3P feed all distillations and pumps were operating.

After 16 hours the set-up reached stable operating conditions. The Rh concentration in the reactor was 280 ppm. A small excess of ligand to rhodium was detectable by liquid chromatography. From that time on ligand was fed to the system by feeding 2 ml an hour of a solution of 2.9 grams of the bidentate phosphite ligand in 360 grams of m-xylene. The concentration of mono methyl adipate was <0.01 wt % at the end of 65 hours of operation. It was found that the conversion of M3P at constant M3P feed rate and hold up time in the reactor dropped during this period of 65 hours continuously from 80% to 75% at a selectivity to M5FV dropping from 82.5 to 81.5%.

After 65 hours 6 grams of the weak acid mono methyl adipate were charged to the system. From that time on until the conclusion of the experiment 100 hours later the conversion of M3P —and thus the activity of the remaining catalyst species—remained constant at 75%. The selectivity to MSFV increased from 81.5% to 82.5%. These results are summarized in Table 1. During the experiment no oxidation of the ligand was found to have occured. At the end of the experiment after 160 hours the tri-ortho-tolyl phosphine was found to be partly oxidized and the ligand concentration was 0.62 mgram/gram of reaction content.

TABLE 1

| reaction time (hours) | 40 | 70 | 165 |
|---|---|---|---|
| ligand/rhodium (mol/mol) | 1.05 | 1.10 | 1.20 |
| mono methyladipate (wt %) | <0.01 | 0.2 | 0.2 |
| conversion of M3P (%) | 79 | 75 | 75 |
| selectivity of methyl 5-formylvalerate (%) | 82.5 | 81.5 | 82.5 |

This example shows that when a continuous process is performed in the presence of a weak acid further deactivation of the catalyst is prevented.

19

Comparative Experiment A

Example 1 was repeated for 160 hours without adding any mono methyl adipate. During the experiment neither oxidation of the ligand nor formation of mono-methyl-adipate by oxidation of methyl 5-formylvalerate was found to have occured. The concentration of mono-methyl-adipate was <0.01 w % throughout the experiment.

At the end of the experiment the tri-ortho-tolyl phosphine was found to be partly oxidized.

It was found that the conversion of M3P at constant M3P feed rate and hold up time in the reactor dropped continuously from 80% to 70% with a selectivity dropping from 82.5% to 81%.

Example 1 and comparison between Example 1 and Experiment A teaches that deactivation of the active catalyst species can be avoided by adding some acid to the process.

EXAMPLE 2

Example 1 was repeated up to 16 hours after start up. The rhodium concentration was 300 ppm. 6.0 grams of mono methyladipate was added to the system. Ligand was fed to the process (in the same composition as described in Example 1) in such a rate that the ligand/rhodium molar ration was kept at a constant value of between 1.1–1.2 (mol/mol). This was done by constantly monitoring the ligand and rhodium concentration and adding fresh ligand to the system when the ligand concentration dropped due to ligand degradation. During the course of the experiment (runtime 260 hours) the conversion remained constant at 81% and the selectivity at 82%. The methyl 5-formylvalerate production was 75.5 grams/hr.

The ligand degradation, determined by the rate of fresh ligand which had to be supplied to the process, is 0.22 grams per kilogram of methyl 5-formylvalerate produced by the process.

EXAMPLE 3

Example 2 was repeated except that the ligand/rhodium molar ratio was kept at a constant value of 3 (mol/mol) at the same rhodium concentration. During the course of the experiment (runtime 260 hours) the conversion remained constant at 78% and the selectivity at 81.5%. The methyl 5-formylvalerate production was 72.3 grams/hr.

The ligand degradation, determined by the rate of fresh ligand which had to be supplied to the process, is 0.96 grams per kilogram of methyl 5-formylvalerate produced by the process.

As can be seen by comparing the rate of ligand degradation of Example 2 and 3 one can see that by performing the process at a slight excess of ligand to rhodium a significantly lower ligand consumption is achieved while the conversion and selectivity is hardly influenced. This is very advantageous, because the ligand cost per amount of methyl 5-formylvalerate can thus be reduced.

What is claimed is:

1. Process for the continuous preparation of an alkyl 5-formylvalerate by reacting an alkyl-3-pentenoate with carbon monoxide and hydrogen by hydroformylation using a catalyst system comprising rhodium and a multidentate organic phosphite ligand according to the formula:

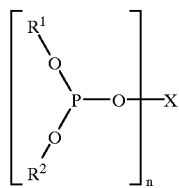

wherein n represents 2–6,

X represents an n-valent organic bridging group, and $R^1$ and $R^2$ represent monovalent aryl groups, wherein the process is carried out in the presence of and acid compound having a pKa between 1 and 12 measured in water at 18° C., and wherein the alkyl group of said alkyl 5-formylvaleriate and alkyl-3-pentenoate comprised from 1 to 20 carbon atoms.

2. Process according to claim 1, wherein the acid is present in an amount of 0.05 to 20 wt %.

3. Process according to any one of claims 1 or 2, wherein $R^1$ and $R^2$ are monovalent aryl groups containing at least one group, $R^3$, other than hydrogen in an ortho position relative to the oxygen atom, where $R^3$ is a $C_1$ to $C_{20}$ alkyl or a $C_6$–$C_{20}$ aryl group.

4. Process according to any one of claims 1 or 2, wherein $R^1$ and $R^2$ are monovalent fused aromatic ring systems with 2 or more rings having 10–20 carbon atoms.

5. Process according to claim 1, wherein the bridging group X is such that the multidentate phosphite ligand can form a chelate-type complex with rhodium or iridium during the reaction conditions.

6. Process according to claim 5, wherein the bridging group X has a structure according to formula (2) or (3):

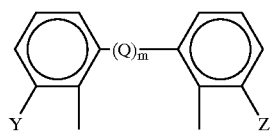

(2)

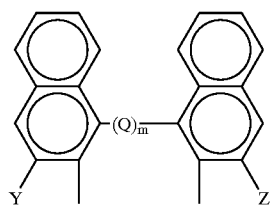

(3)

in which Q is —O—, —S— or a —$CR^4R^5$— divalent group and m is 0 or 1 and $R^4$ and $R^5$ is hydrogen or a methyl group and Y and Z hydrogen or organic groups containing at least one carbon atom.

7. Process according to claim 6, wherein Y and Z are individually a carboalkoxyl or a carboaryloxy group, —$CO_2R^6$, in which $R^6$ is a $C_1$–$C_{20}$ alkyl group or a $C_6$–$C_{12}$ aryl group.

8. Process according to claim 6, wherein the bridging group is a 1,1'-binaphthalene bridging group according to formula (3).

9. Process according to claim 1, wherein rhodium is part of the catalyst system.

10. Process according to claim 1, wherein the alkyl 3-pentenoate is present in a mixture of alkyl pentenoates having a composition of 0–10% alkyl 2-pentenoate, 0–30% alkyl 4-pentenoate and 60–100% 3-pentenoate in which the total of alkyl pentenoates add up to 100%.

11. Process according to claim 1, wherein the molar ratio of multidentate phosphite ligand to rhodium is between 1–1.2.

12. Process according to claim 1, wherein the process is carried out in the presence of an organophosphorous ligand which has a coordination strength to rhodium less than the multidentate organic phosphite ligand.

13. Process according to claim 1, wherein the process is performed by continuously removing part of the liquid reaction medium, comprising the alkyl 5-formylvalerate, the catalyst system, optionally the solvent, by-products, unreacted alkyl pentenoate and carbon monoxide and hydrogen dissolved in said medium from a hydroformylation reactor, removing carbon monoxide and hydrogen from this mixture by reducing the pressure, separating alkyl 5-formylvalerate, unreacted alkyl pentenoate and low boiling by-products from the catalyst system in one or more distillation operations performed at reduced pressure and recycling the catalyst system to the hydroformylation reactor.

14. Process according to claim 13, wherein the recirculating catalyst system is contacted with an ionexchanger having basic groups.

* * * * *